(12) United States Patent
Vaidya

(10) Patent No.: US 8,609,003 B2
(45) Date of Patent: Dec. 17, 2013

(54) APPARATUS AND METHOD FOR FORMING AN ANTIBIOTIC IMPREGNATED BONE CEMENT INTRAMEDULLARY NAIL

(76) Inventor: Rahul Vaidya, Tecumseh (CA)

(*) Notice: Subject to any disclaimer, the term of this patent is extended or adjusted under 35 U.S.C. 154(b) by 261 days.

(21) Appl. No.: 13/134,904

(22) Filed: Jun. 21, 2011

(65) Prior Publication Data

US 2012/0089148 A1    Apr. 12, 2012

Related U.S. Application Data

(60) Provisional application No. 61/404,737, filed on Oct. 12, 2010.

(51) Int. Cl.
*A61B 17/72* (2006.01)
*B29C 45/14* (2006.01)
*B29D 99/00* (2010.01)

(52) U.S. Cl.
USPC .......... 264/275; 249/91; 425/117; 425/129.1; 606/62; 606/64

(58) Field of Classification Search
USPC ........ 425/117, 129.1; 249/55, 83, 91; 606/62, 606/63, 64; 264/275
See application file for complete search history.

(56) References Cited

U.S. PATENT DOCUMENTS

| | | | | |
|---|---|---|---|---|
| 1,745,482 | A * | 2/1930 | Goodwin | 425/129.1 |
| 4,824,627 | A * | 4/1989 | Hammer et al. | 249/91 |
| 5,514,137 | A * | 5/1996 | Coutts | 606/62 |
| 5,618,286 | A * | 4/1997 | Brinker | 606/62 |
| 6,155,812 | A * | 12/2000 | Smith et al. | 249/55 |
| 6,551,321 | B1 * | 4/2003 | Burkinshaw et al. | 606/62 |
| 7,637,729 | B2 * | 12/2009 | Hartman et al. | 249/55 |
| 7,789,646 | B2 * | 9/2010 | Haney et al. | 425/117 |
| 8,480,389 | B2 * | 7/2013 | Haney et al. | 425/117 |

* cited by examiner

*Primary Examiner* — Robert B Davis
(74) *Attorney, Agent, or Firm* — David W. Schumaker

(57) ABSTRACT

A method and apparatus for forming any size antibiotic impregnated bone cement (AIBC) intramedullary (IM) nail. The cement nail is formed around a base support or base IM nail. The apparatus includes a molded plastic tube device to form the shape of the cement IM nail and plastic spacers which position the molded plastic tube around the base support or base IM nail for formation of the cement nail. The AIBC material may be any of the known antibiotic loaded/impregnated bone cements that are commercially available.

20 Claims, 18 Drawing Sheets

APPARATUS AND METHOD FOR FORMING AN ANTIBIOTIC IMPREGNATED BONE CEMENT INTRAMEDULLARY NAIL

CROSS-REFERENCE TO RELATED APPLICATIONS

This application claims benefit of priority to U.S. Provisional Application Ser. No. 61/404,737 filed Oct. 12, 2010, which is incorporated herein by reference in its entirety.

FIELD OF THE INVENTION

The present invention relates generally to IM nailing of fractured long bones, and more specifically to IM nailing of fractured long bones using antibiotic impregnated bone cement (AIBC) intramedullary IM nails. The invention specifically discloses a method and apparatus for simply and efficiently forming any size AIBC IM nail.

BACKGROUND OF THE INVENTION

Rod or nail placement in the medullary cavity for securing bone fractures is a common practice in orthopedic surgery. Use of the rod is known to inherently produce better healing in more extreme fractures than other procedures in which the rod is omitted. Spanning the fracture zone, the rod imposes a rigidity to the fracture area that could otherwise be difficult to maintain during the prolonged period of mending. When left permanently in place, the rod reinforces the bone and reduces its susceptibility to refracture.

The interlocking intramedullary nail has been widely used in the treatment of long bone fractures in recent years. However, patients who suffered from infection after nailing are hard to deal with. The current management of this kind of infection consists of two main objectives, one of which is infection control, which usually is achieved by nail removal with debridement, lavage of the medullary canal and local delivery of antibiotics. Unfortunately, removal of the intramedullary nail causes a high risk of non-union or additional fractures, challenging surgeons to prevent such fractures with few guidelines for how this can be done. Generally, external fixation is substituted for the removed IM nail.

To fight the infection, antibiotic-impregnated beads have been used to fill the dead space and deliver high concentration of specific antibiotics to the infected sites simultaneously, but some defects limit the application of antibiotic beads. Specifically, filling dead space incompletely, being hard to take out, and a short period of implantation time. These beads have been replaced by antibiotic spacers, and antibiotic PMMA-coated guide rods. While these methods address the problem of infection, all of these methods are temporary and provide no significant stability to the fracture, except for the antibiotic PMMA-coated guide rods, which provide limited stability to axial and bending forces but no rotational stability. Essentially, none of these methods results in stability that is comparable to a locked intramedullary nail, and none is likely to consistently achieve bony union without a subsequent procedure. For this reason, surgeons have started using antibiotic impregnated PMMA bone cement (AIBC) coated IM nails to treat an infected long bone fractures.

Current methods for creating these coated nails are hap hazzard, involving make-shift molds or cumbersome and costly metal molds. The methods are slow and difficult and generally the coated IM nails require removal of excess bone cement such as cutting away the bone cement that oozes out between mold halves or drilling our the bone cement that fills the locking hardware holes. Thus, there is a need in the art for a simple, inexpensive kit for forming AIBC IM nails of any size, and a method for simply forming them.

SUMMARY OF THE INVENTION

The present invention is a kit and method for forming antibiotic impregnated bone cement (AIBC) intramedullary (IM) nails. The kit for forming antibiotic impregnated bone cement (AIBC) intramedullary (IM) nails may include a molded tube, the molded tube may have an interior shape and size corresponding to the desired final AIBC IM nail and mau include an attachment means at one end thereof to allow for attachment of the molded tube to a conventional bone cement gun, the other end of the molded tube may be adapted to allow for insertion of a base support or base IM nail thereinto.

The kit may further include mold spacers which may be adapted to either:

1) be inserted into locking screw holes of the base support or base IM nail; the mold spacers may allow the base IM nail to be properly spaced in the center of the molded tube so that AIBC can be evenly distributed around the base IM nail within the molded tube as the AIBC is pumped in by the cement gun; or 2) form locking screw holes in the final AIBC IM nail when the base support does not have locking screw holes.

The molded tube may have a length which accommodates a specific base support or base IM nail. Alternatively, the molded tube may have a length which is longer than needed to accommodate any specific base support or base IM nail and may be cut to the required length of the desired final AIBC IM nail. Furthermore, the molded tube may have indicia thereon to indicate where to cut the molded tube to the desired length. The molded tube may have an inner diameter which corresponds to the desired diameter of the final AIBC IM nail. The inner diameter may be selected from the group consisting of 9, 10, 11, 12, 13, and 14 mm. The molded tube may be formed from a material that is: 1) compatible with the AIBC, 2) easily holds it's shape, and 3) is easily removed from the finished, hardened AIBC IM nail.

The mold spacers may be designed to keep the AIBC from plugging the locking screw holes of the base support or base IM nail. The mold spacers may be small tubes or cylinders that have an outer diameter equal to the inner diameter of the locking screw holes of the base support or base IM nail and a length equal to the inner diameter of the molded tube. The mold spacers may be integrally formed into the molded tube and extend into the interior of the molded tube far enough to plug the locking screw holes of the base support or base IM nail.

The kit may further include a supply of AIBC. The kit may also further include a base support or a base IM nail. The base support may not be adapted to be attached to an IM nail insertion handle and thus the kit may further include a proximal end stub of a conventional IM nail, which may be inserted in the proximal end of the molded tube and hardened into the AIBC to provide the AIBC IM nail with a means for attachment to IM nail insertion hardware.

The base support may be a metal strip or metal plate. The base support may also be at least one of the group consisting straight wires, curved wires, coils, flat mesh, and mesh cages.

The kit may also include a bone cement gun, and may further include locking screws or other hardware for fixation of the final AIBC IM nail as well as IM nail insertion hardware.

The inventive method for forming an antibiotic impregnated bone cement (AIBC) intramedullary (IM) may include the step providing a molded tube, the molded tube may have an interior shape and size corresponding to the desired final AIBC IM nail and may include an attachment means at one end thereof to allow for attachment of the molded tube to a conventional bone cement gun, the other end of the molded tube may be adapted to allow for insertion of a base support or base IM nail thereinto. The method may also include the step of providing a base support or base IM nail which will form the support for the AIBC IM nail;

The method may further include the step of providing mold spacers adapted to either:

1) be inserted into locking screw holes of the base support or base IM nail; the mold spacers may allow the base IM nail to be properly spaced in the center of the molded tube so that AIBC can be evenly distributed around the base IM nail within the molded tube as the AIBC is pumped in by the cement gun; or 2) form locking screw holes in the final AIBC IM nail when the base support does not have locking screw holes.

The method may also include the step of providing a bone cement gun loaded with AIBC. Further, if the base support or base IM nail has locking screw holes, then the method may include the step of inserting the mold spacers into the locking screw holes, wherein the mold spacers protrude substantially equidistant from either side of the base IM nail.

The method also may include the step of inserting the base support or base IM nail into the end of the molded tube that is adapted for insertion of the base support or base IM nail thereinto and may also include the step of attaching the molded tube to the bone cement gun via the attachment means thereon, wherein the attaching step may occur before or after the step of inserting the base support or base IM nail into the molded tube.

The method may include the further steps of pumping AIBC from the cement gun through the attachment means into the interior of the molded tube, removing the molded tube from the cement gun and allowing the AIBC to set or harden. Once the AIBC has hardened, the method may further include the step of removing the molded tube and the mold spacers from the AIBC IM nail.

The mold spacers may be small tubes or cylinders and the base support or base IM nail may have locking screw holes, in which case the mold spacers may have an outer diameter equal to the inner diameter of the locking screw holes of the base support or base IM and a length equal to the inner diameter of the molded tube. The mold spacers may substantially prevent the AIBC from being pumped into the locking screw holes of the base support or base IM. In this embodiment of the inventive method, the step of inserting the mold spacers into the locking screw holes occurs before the step of inserting the base support or base IM nail into the molded tube.

Alternatively, the mold spacers may be small protrusions molded into the interior of the molded tube and the base support or base IM nail has locking screw holes. The mold spacers may protrude from the interior wall of the molded tube and plug the locking screw holes of the base support or base IM nail, thereby substantially preventing the AIBC from being pumped into the locking screw holes of the base support or base IM nail. In this embodiment the step of inserting the mold spacers into the locking screw holes occurs after the step of inserting the base support or base IM nail into the molded tube.

In yet another embodiment, the mold spacers may be small protrusions molded into the interior of the molded tube and the base support does not have locking screw holes. In this case the mold spacers may protrude from the interior wall of the molded tube and extend across the entire diameter of the molded tube, thereby forming locking screw holes in the final AIBC IM nail by substantially preventing the AIBC from being pumped into the volume occupied by the mold spacers.

The method may further include the step of trimming any excess length off from the molded tube, either prior to or after the step of inserting the base support or base IM nail into the molded tube. The pumping step may include pumping a sufficient amount of the AIBC to completely surround the base support or base IM nail and fill the entire interior of the molded tube. The method may also include the steps of preparing the AIBC and loading the prepared AIBC into the cement gun. The step of removing the molded tube and mold spacers from the AIBC IM nail may include one or more of cutting, tearing, pealing and sliding the molded tube.

These and other objectives are satisfied by the method and kit/apparatus described hereinafter.

BRIEF DESCRIPTION OF THE DRAWINGS

FIGS. 17a-16c depict a cross-section of molded tube 4 with integrally formed mold spacers and a base IM nail;

DETAILED DESCRIPTION OF THE INVENTION

The present invention relates to a method and apparatus for forming any size antibiotic impregnated bone cement (AIBC) intramedullary (IM) nail. The cement nail is formed around a base support, which could be a conventional metal IM nail. The apparatus includes a molded plastic tube device to form the shape of the cement nail around the base support (hereinafter also called just "base") and plastic spacers which position the molded plastic tube around the base for formation of the cement nail. The AIBC material may be any of the known antibiotic loaded/impregnated bone cements that are commercially available.

Figure 1:
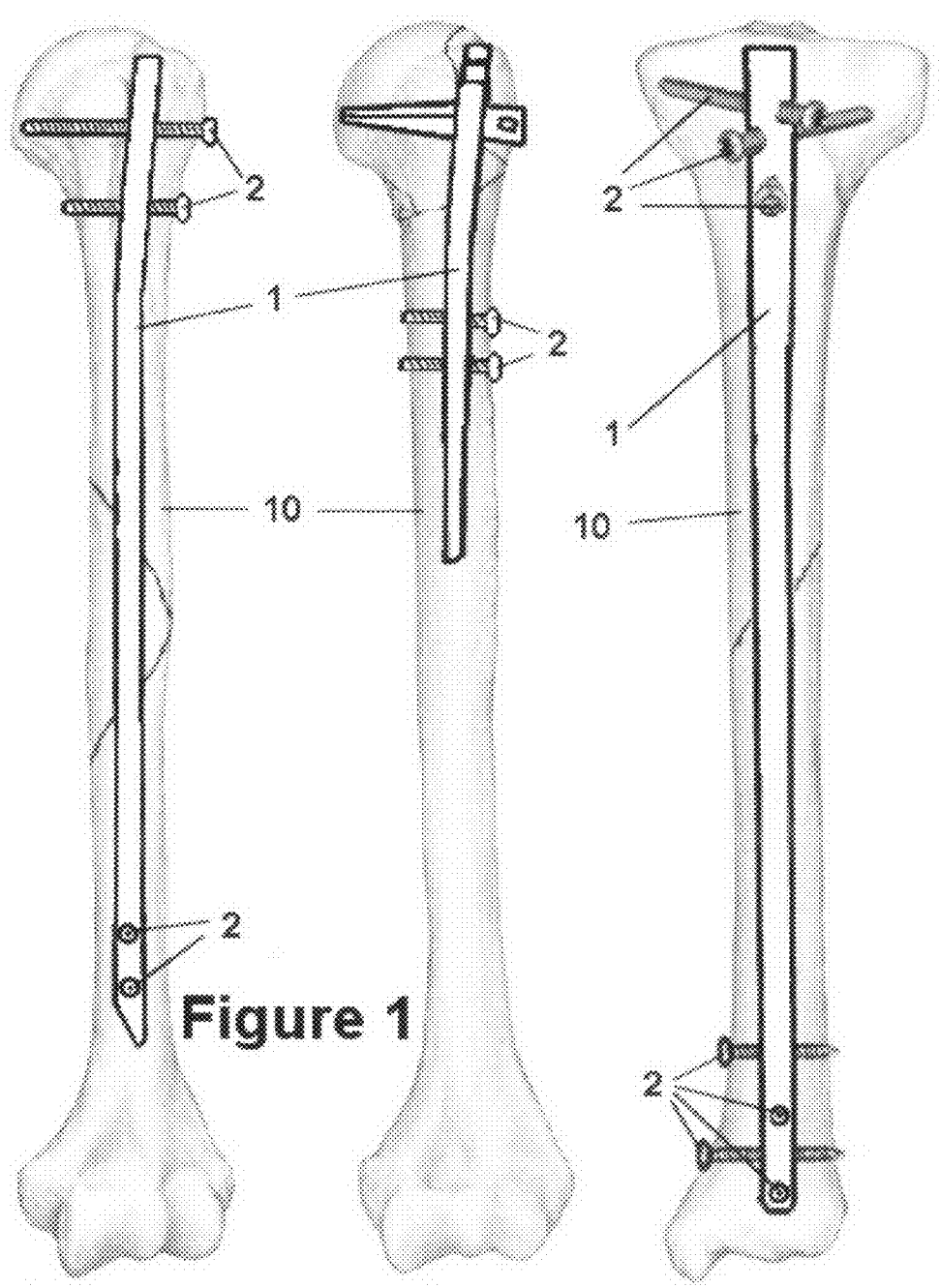
FIG. 1 shows typical metal IM nails 1 inserted into fractured long bones 10 and shows locking screws 2 usually associated with IM nails.

FIG. 1 shows typical metal IM nails 1 inserted into fractured long bones 10 and shows locking screws 2 usually associated with IM nails. There are many different types of IM nails 1 specific to the fractured bone 10 being nailed and the position of the fracture of the bone. Within this invention, any conventional IM nail may be used as the base nail onto which AIBC is formed using the method and apparatus of the present invention. The cement nails produced by the method and apparatus of the present invention may be used to nail the femur, humerus, or tibia.

Alternatively, special IM nails may be made specifically to form the base of the AIBC covered nail. Thus, the specially made IM nail may be thinner than a normal IM nail, such that when the AIBC is molded onto the specially made nail, the final coated nail is the size of a normal IM nail without the coating, if desired.

Figure 2:
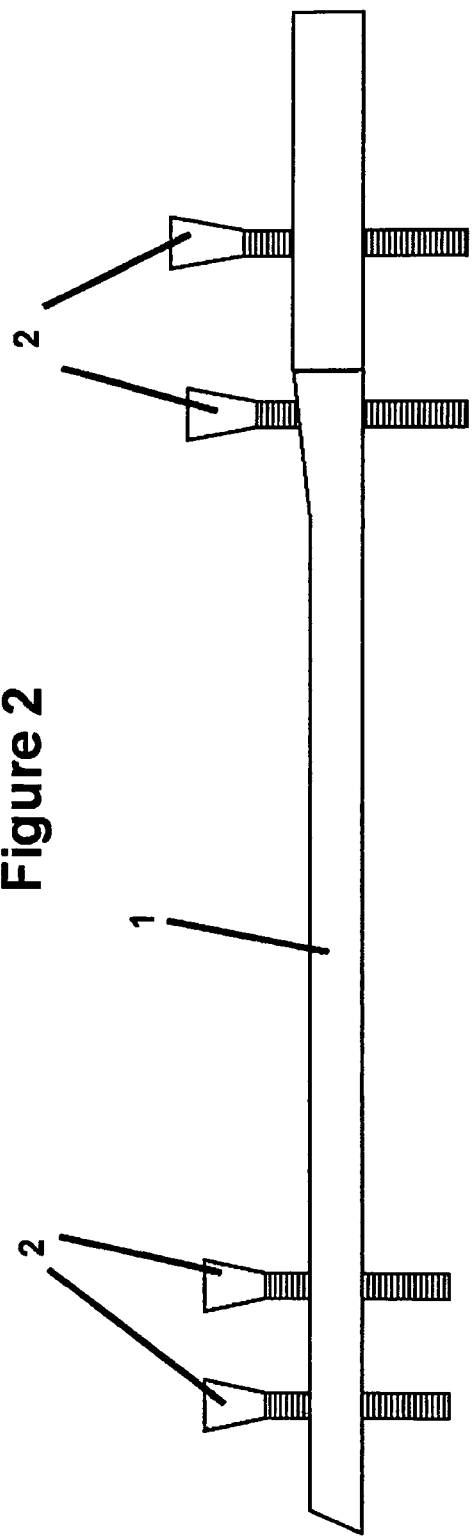
FIG. 2 is a stylized depiction of a typical metal IM nail 1, and specifically shows the manner in which the locking screws 2 may be inserted.

FIG. 2 is a stylized depiction of a typical metal IM nail 1, and specifically shows the manner in which the locking screws 2 may be inserted. The IM nail may be formed of a metal such as titanium alloys or biocompatible steel alloys, etc. The length of the IM nail depends on the specifics of the bone to be nailed and the position of the fracture.

Figure 3:
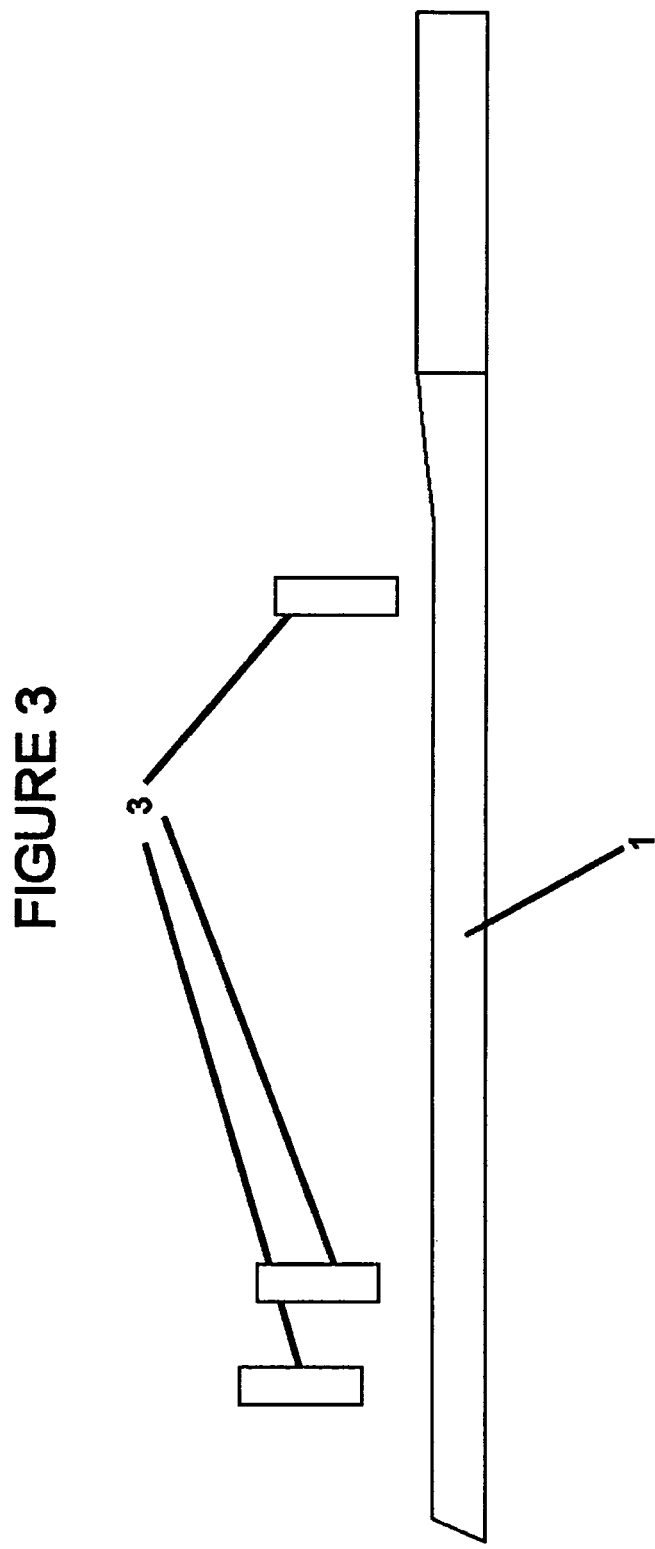
FIG. 3 shows the metal IM nail with mold spacers 3 of the present invention.
Figure 4:
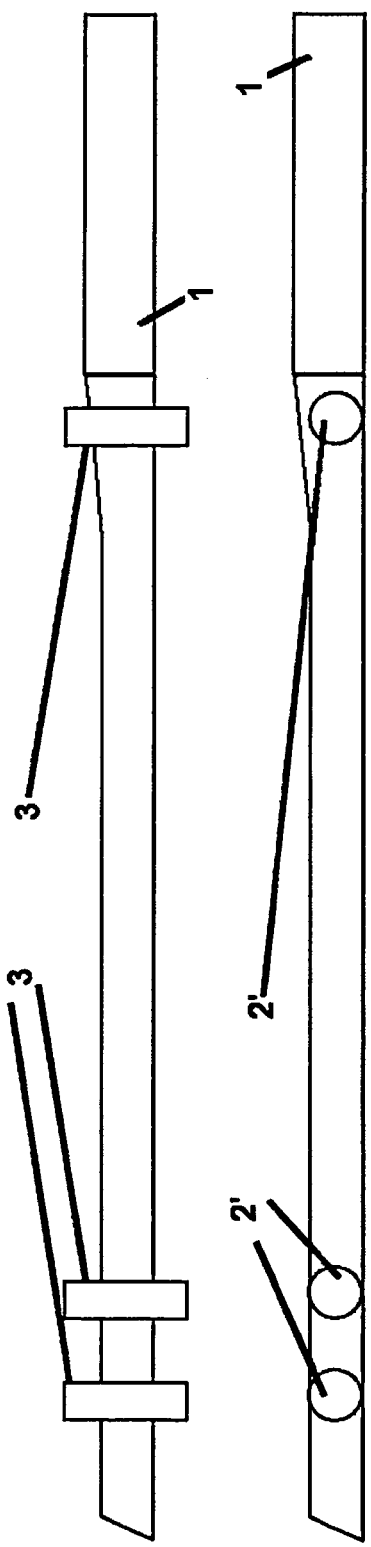
FIG. 4 shows how the mold spacers 3 fit into the locking screw holes of a base metal IM nail.

FIG. 3 shows the base metal IM nail with mold spacers 3 of the present invention. The mold spacers 3 are inserted into the locking screw holes 2' of the metal IM nail 1 and act as centering aids for the plastic molded tube which is to be placed over the metal IM nail 1 (and optionally the mold spacers 3). FIG. 4 shows how the mold spacers 3 fit into the locking screw holes on the base metal IM nail.

Figure 5:
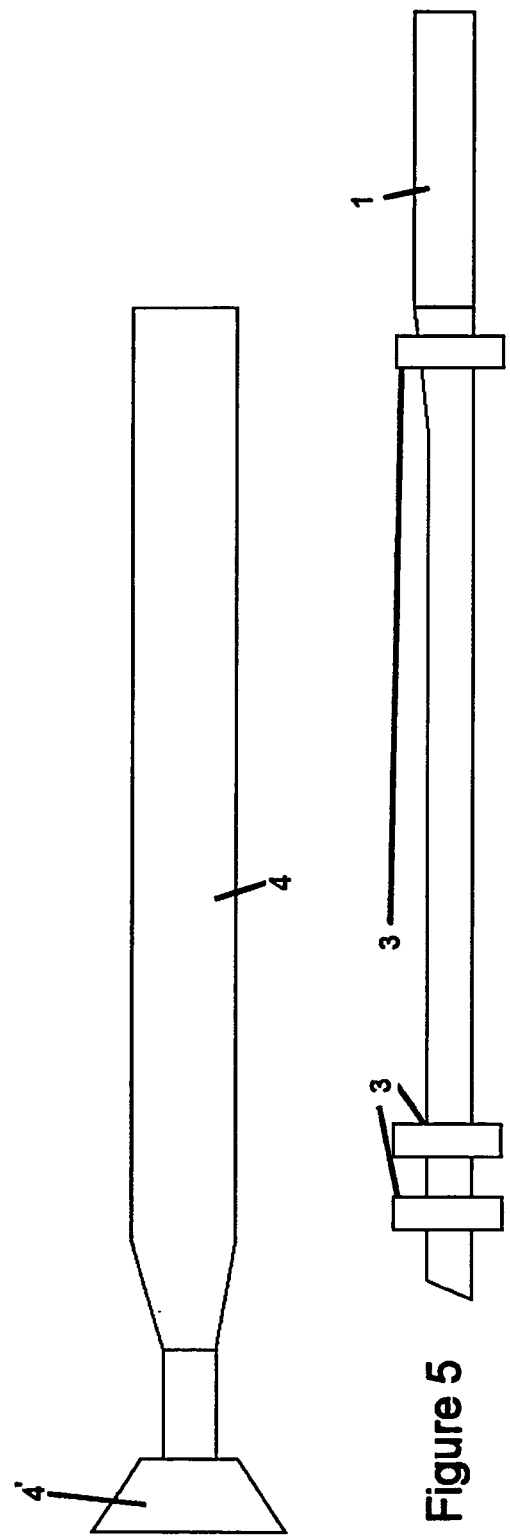
FIG. 5 shows the molded plastic tube 4 of the present invention and a base metal IM nail 1 with the mold spacers 3 inserted into the locking screw holes 2'.
Figure 6:
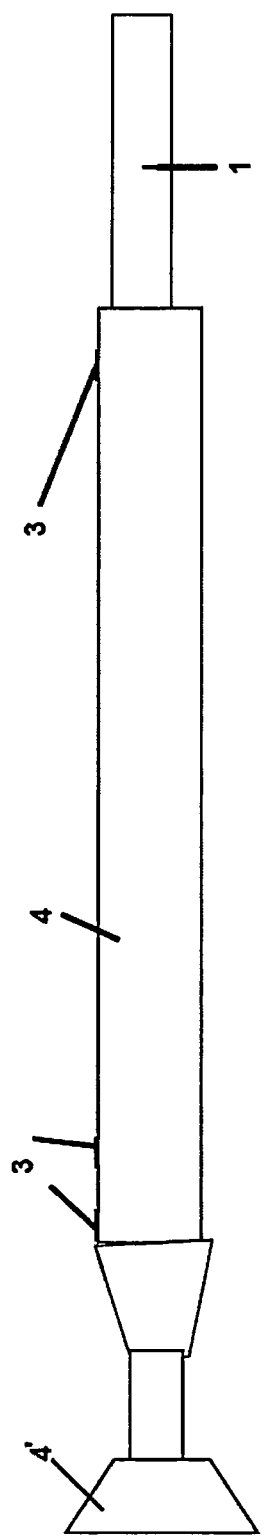
FIG. 6 depicts the manner in which the mold spacers 3 center the molded tube 4 over the base metal IM nail 1.

FIG. 5 shows the molded plastic tube 4 and the base metal IM nail 1 with the mold spacers 3 inserted into the locking screw holes 2'. The molded tube 4 has a long hollow tubular end that fits over the metal IM nail 1 and the mold spacers 3. The spacers center the tube 4 over the metal IM nail 1 as shown in FIG. 6. One end of the tube 4 includes an attachment means 4' to allow the tube to be attached to a conventional bone cement gun 5.

Figure 7:
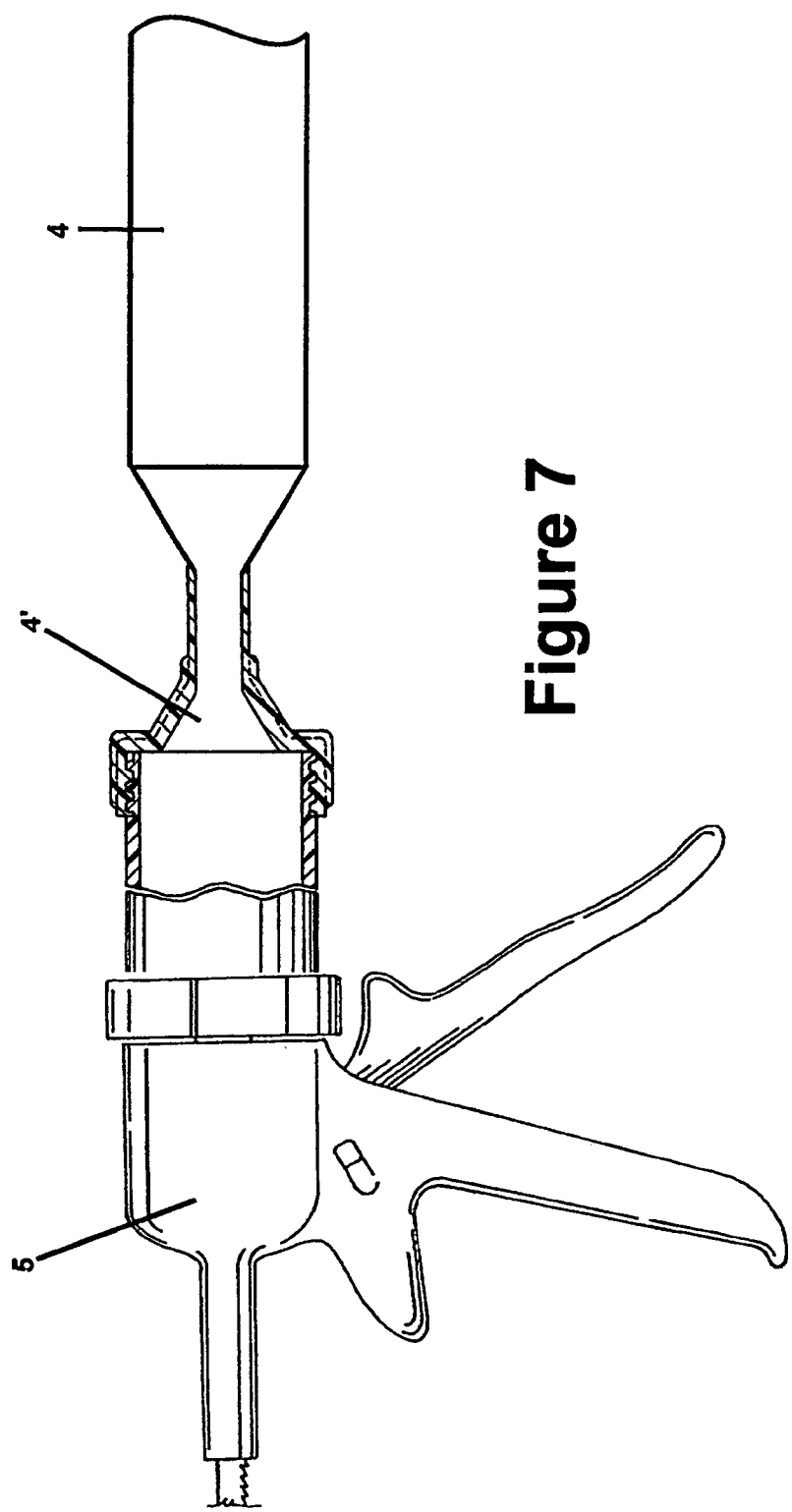
FIG. 7 depicts how the molded tube 4 is attached to a conventional cement gun 5 via attachment means 4'.

As shown in FIG. 7, once the molded tube 4 is placed around the base metal IM nail 1 and the mold spacers 3, the tube 4 is attached to a conventional cement gun via attachment means 4'. Thereafter, the space within the molded tube 4 between the tube inner wall and the base metal IM nail 1 is pumped full of AIBC.

Figure 8:
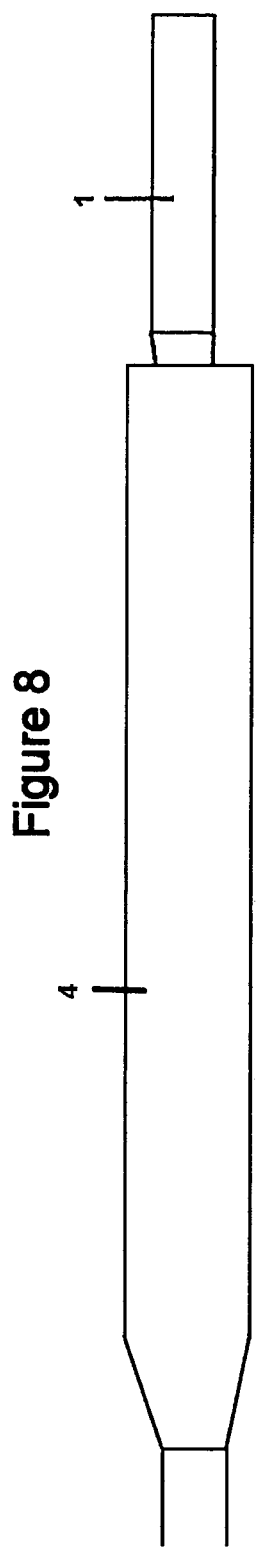
FIG. 8 shows that the tube/AIBC/base metal IM nail combination is removed from the cement gun 5 once the tube is filled with AIBC and the AIBC is allowed to set/harden.
Figure 9:
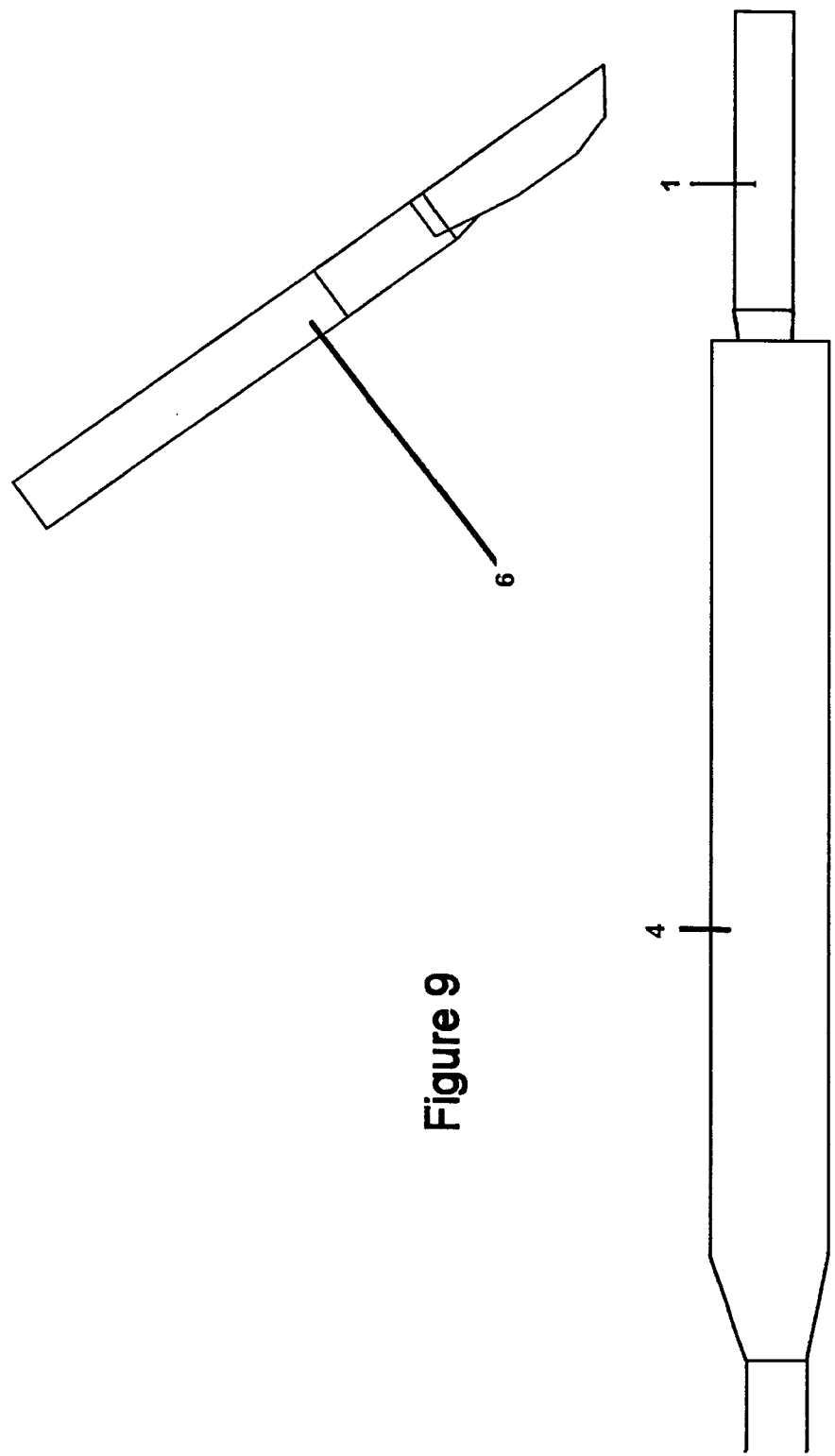
FIG. 9 shows how the molded tube 4 may be removed from the AIBC IM nail by cutting the tube 4 from the cement nail 7 with a knife 6.

The tube/AIBC/base metal IM nail combination is removed from the cement gun 5 and the AIBC is allowed to set/harden (See FIG. 8). Once the AIBC is hardened, the molded tube 4 is removed. This may be accomplished by cutting the tube 4 from the cement nail 7 with a knife 6 as shown in FIG. 9. Alternatively, the molded tube may include perforations and/or other means to allow the tube to be removed without the need for cutting.

Figure 10:
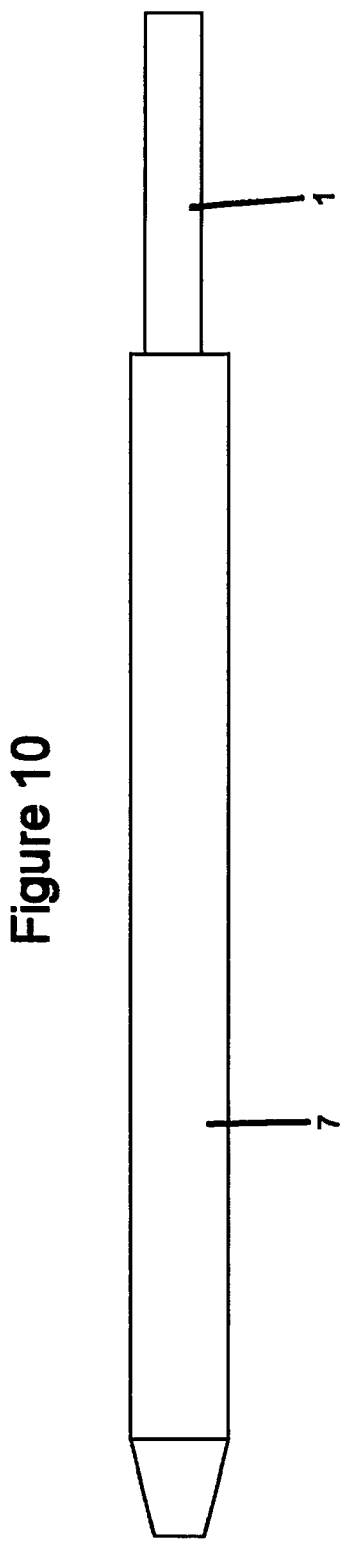
FIG. 10 shows the final AIBC nail 7 now hardened and formed about the base metal IM nail 1.
Figure 11:
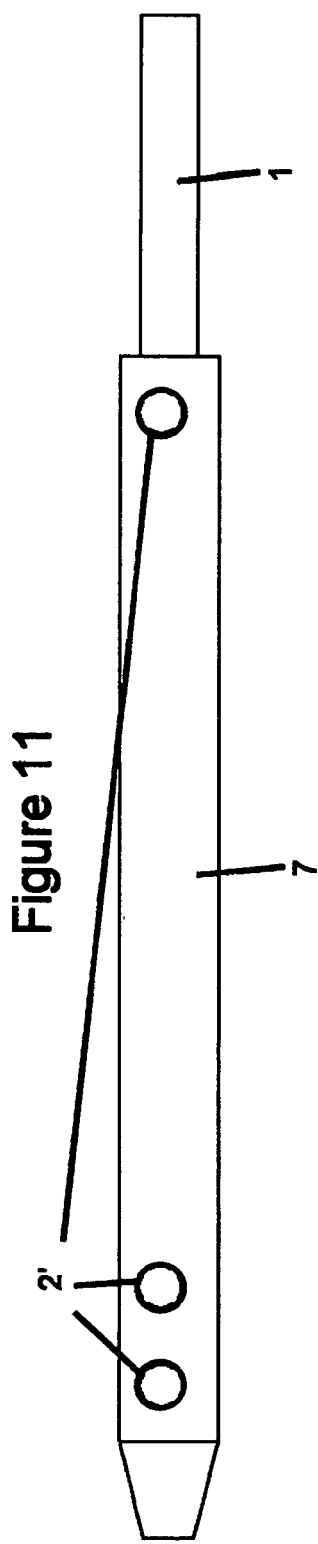
FIG. 11 depicts the manner in which the mold spacers 3 are removed to reveal the locking screw holes 2' to allow for proper placement of the locking hardware (such as locking screws 2) once the nail is placed into a fractured bone.

FIG. 10 shows the AIBC nail 7 now hardened and formed about the base metal IM nail 1. Preferably the end of the IM nail that attached to the insertion handle 8 is free from AIBC. It should be noted that at this point the mold spacers 3 are still in the locking screw holes 2' and are surrounded by AIBC. Therefore, the mold spacers 3 must be removed to reveal the locking screw holes 2' to allow for proper placement of the locking hardware (such as locking screws 2) once the nail is placed into a fractured bone 10 (see FIG. 11).

Figure 12:
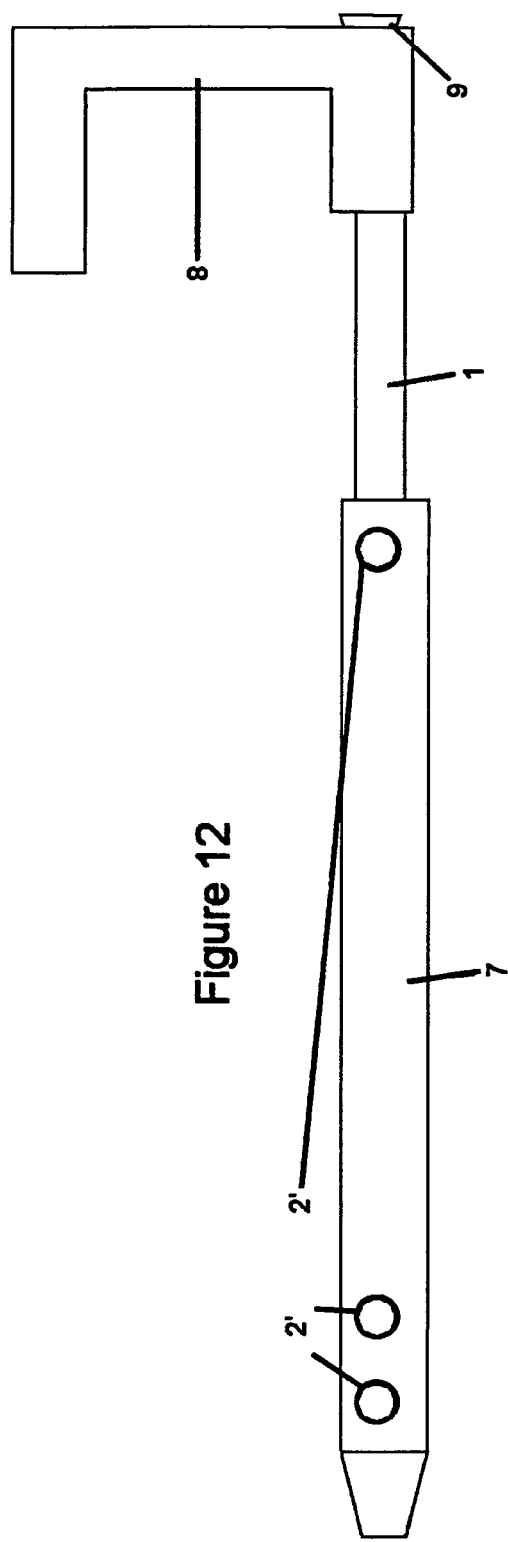
FIG. 12 depicts a conventional insertion handle 8 attached to the cement nail using a conventional attachment screw 9.
Figure 13:
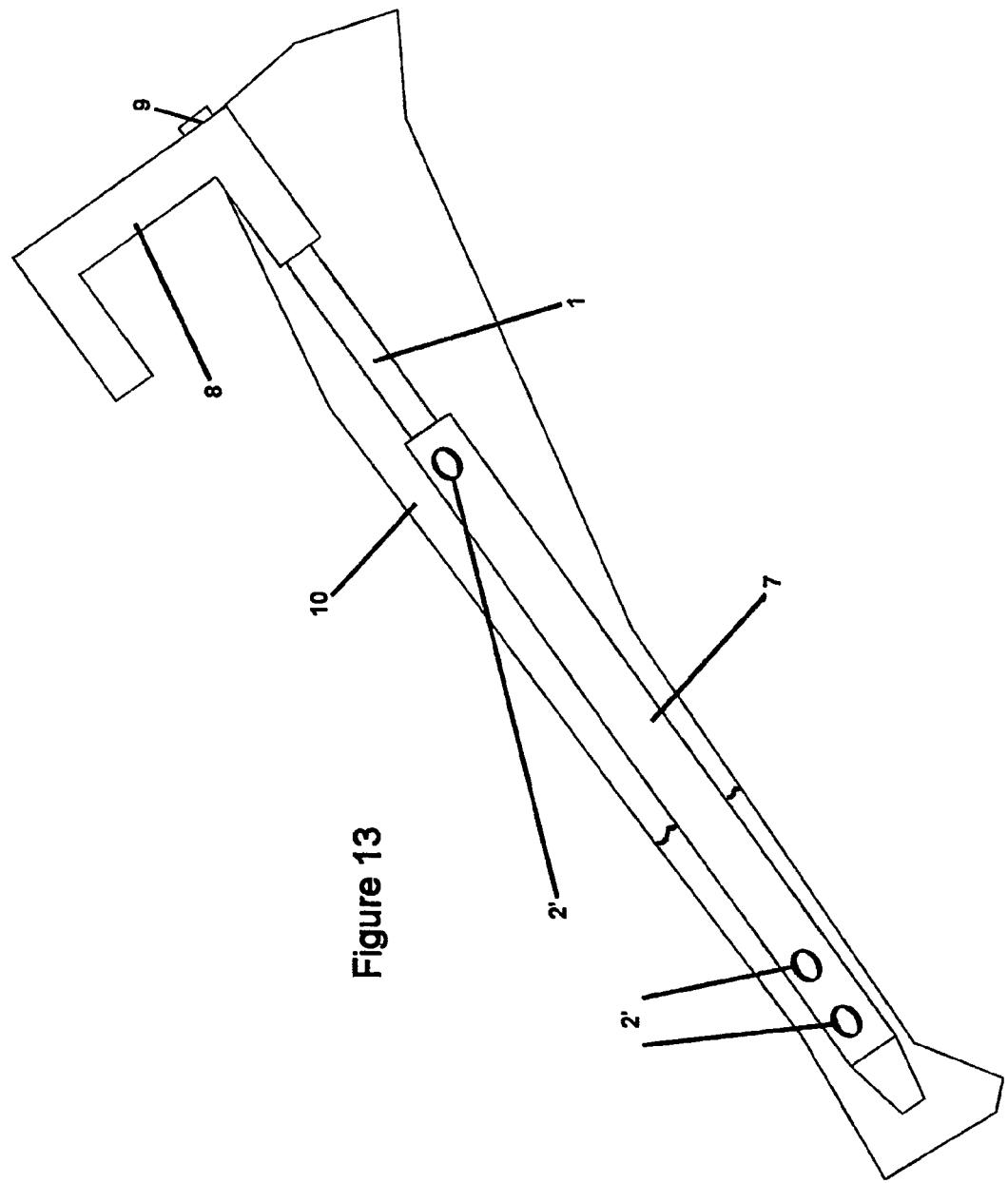
FIG. 13 depicts the manner in which the nail may be placed into a fractured bone 10 as needed using locking screws 2, placed in locking screw holes 2' as is conventional.

Once the cement nail is ready, a conventional insertion handle 8 can be attached using a conventional attachment screw 9 (see FIG. 12) and the nail may be placed into a fractured bone 10 as needed (see FIG. 13) using locking screws 2, placed in locking screw holes 2' as is conventional.

As an alternative, instead of the base metal IM nail, the cement nail can be formed on other base/support elements. For example, the base may be a metal strip or plate with holes through the strip in the proper locations to allow for spacers to create locking screw holes in the molded cement nail. Another alternative may be metal wires, such as straight or curved wires, coils, flat mesh, or mesh cages. The metal wires act like reinforcing steel bar in concrete structural constructions. This wire structure is useful because the cement nail alone (without the support) is strong in compression, but is weak in tension. Thus the base provides added tension strength to the cement nail. While metal wire is described above, other materials may be used to form the support as long as it adds to the strength of the cement nail. If the base support is not adapted to be attached to an IM nail insertion handle, then the kit of the present invention includes a proximal end stub of a conventional IM nail. This stub is inserted into the proximal end of the molded tube and hardens in place in the AIBC to provide the AIBC IM nail with a means for attachment to IM nail insertion hardware.

Figure 14:
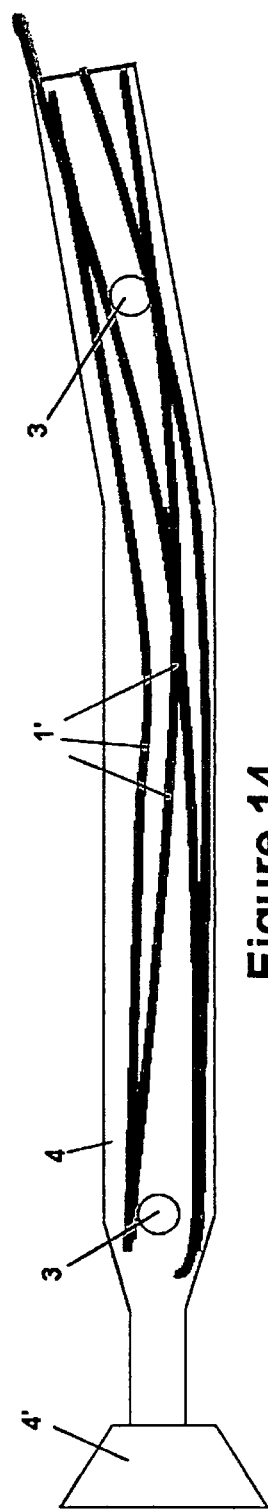
FIG. 14 shows a molded tube 4 of the present invention having wires 1' inserted therein to form the base of the cement IM nail.
Figure 15:
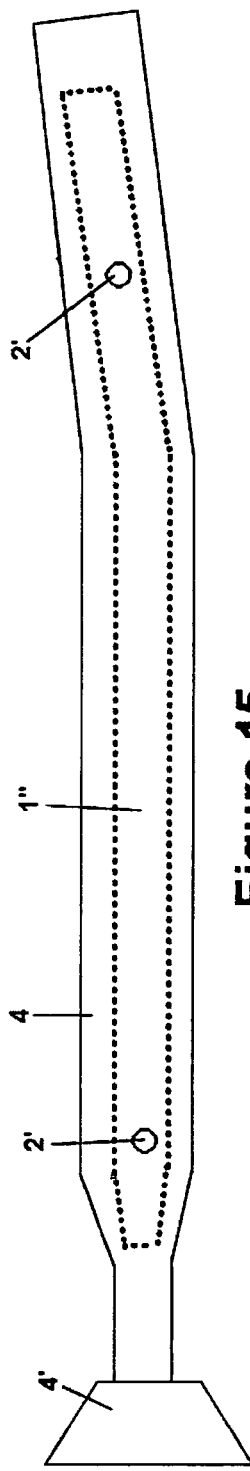
FIG. 15 shows a molded tube 4 of the present invention having a metal plate or strip 1" inserted therein to form the base of the cement IM nail.

FIG. 14 shows a molded tube 4 of the present invention having wires 1' inserted therein to form the base of the cement nail. FIG. 15 shows a molded tube 4 of the present invention having a metal plate or strip 1" inserted therein to form the base of the cement IM nail. The metal strip 1" has locking screw holes 2' into which mold spacers (not shown) may be placed to center the strip in the molded tube 4.

Figure 16A:
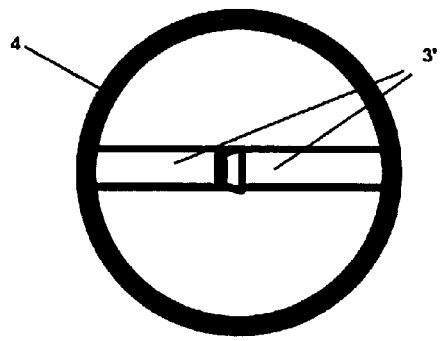
FIGS. 16a-16d depict a cross-section of molded tube 4 with integrally formed mold spacers and various base supports.
Figure 16B:
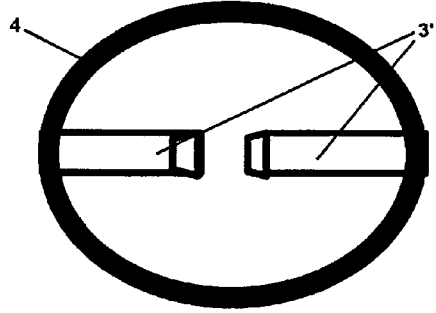
Figure 16C:
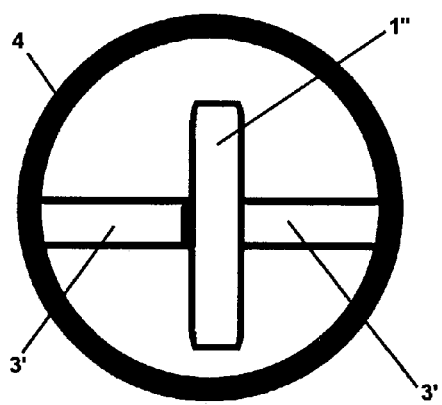
Figure 16D:
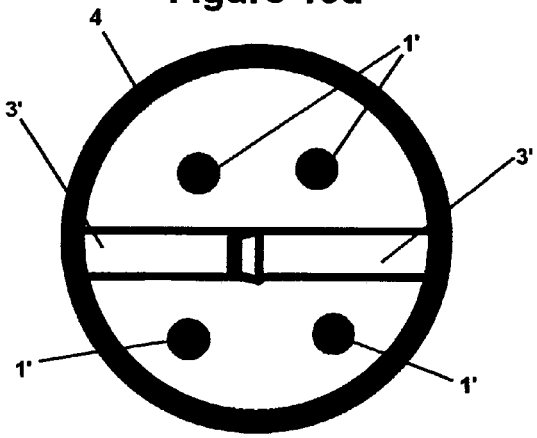

It should be noted that while the mold spacers 3 have been described above as separate components, the mold spacers may alternatively be integrally formed into molded tube 4. FIG. 16a is a cross-section of molded tube 4, depicting the integrally formed mold spacers 3'. These mold spacers 3' may extend partially into the molded tube 4 or may extend fully into the tube such that the end of a spacer on one side of the tube fits into the corresponding end of an opposite spacer on the other side of the tube. When the spacers extend fully across the tube they may be designed to separate when the molded tube is compressed, this can be seen in FIG. 16b. This separation allows for a nail base such as a metal strip or plate 1" to be inserted between the mold spacers 3'. When compression on the molded tube 4 is released, the mold spacers 3' plug the has locking screw holes 2' in the metal strip or plate 1" as is shown in FIG. 16c. Mold spacers 3' which together extend all the way across the diameter of the molded tube 4 are also useful when the nail base is one or more wires 1' as described above. This is depicted in FIG. 16*d* which is a cross section of a molded tube 4 having integral mold spacers 3' and wires 1' as a nail base.

Figure 17A:
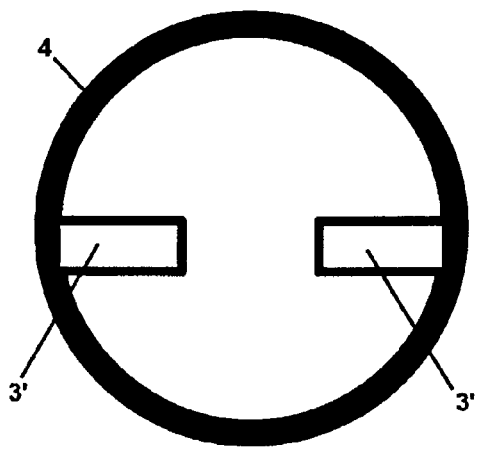
Figure 17B:
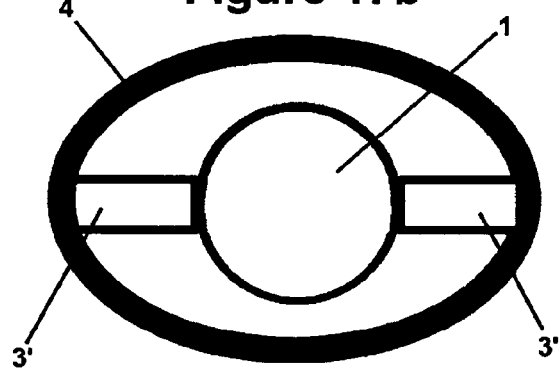
Figure 17C:
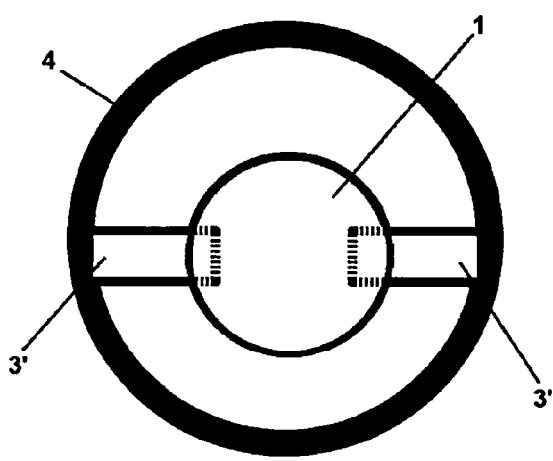

In the case where the integral mold spaces 3' do not extend fully across the molded tube 4, as shown in FIG. 17*a*, the nail base can be a large rod or an actual metal IM nail. The molded tube 4 can be compressed to further separate the integral mold spacers 3' allowing for insertion of the nail base 1 as shown in FIG. 17*b*. Once the metal IM nail 1 or similar nail base is in place the compression on the molded tube 4 can be released and the mold spacers 3' can be inserted into the locking screw holes 2' of the metal IM nail 1 as is depicted in FIG. 17*c*.

Figure 18:
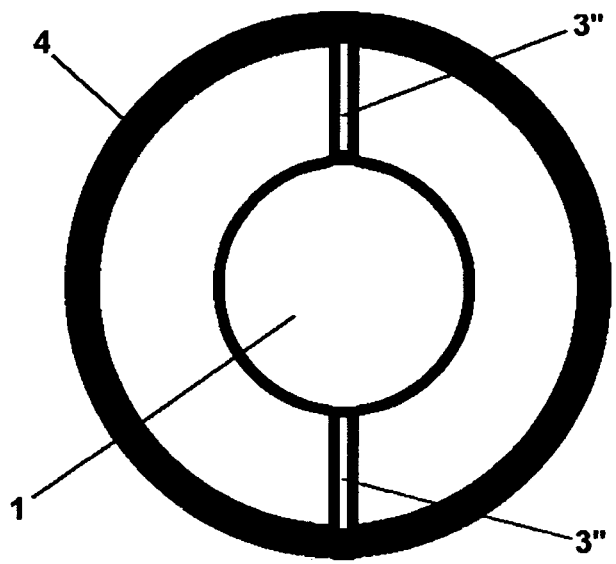
FIG. 18 depicts a cross-section of molded tube 4 with additional mold spacers 3" which are only designed to properly center the nail base.
Figure 19:
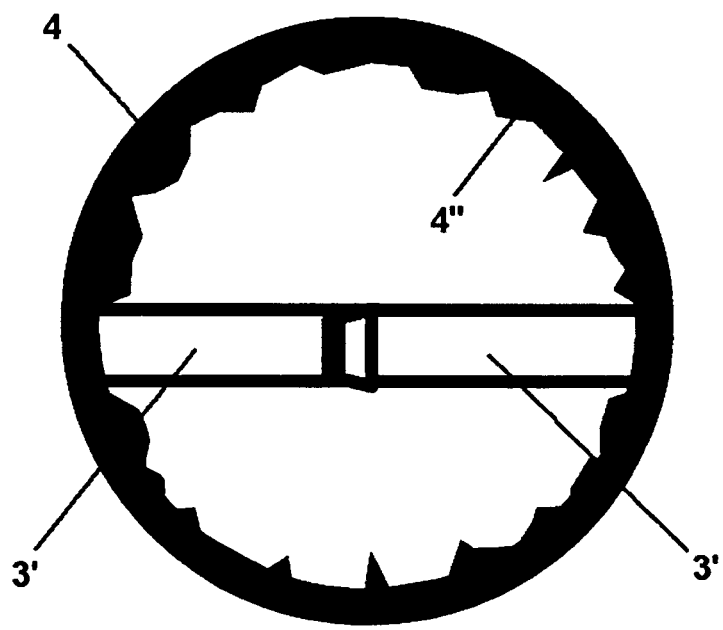
FIG. 19 depicts a cross-section of molded tube 4 showing how the inner wall of the tube may be corrugated, roughened or otherwise shaped, to provide a greater surface area to elute the antibiotic impregnated in the bone cement of the cement nail.

In addition to the mold spacers 3 and 3' described above, which are used to create and/or protect locking screw holes 2' of the cement IM, additional mold spacers 3" which are only designed to properly center the nail base (see FIG. 18). The additional mold spacers 3" do not extend the length of the molded tube 4, as this would cause a deep slot in the nail and make it unstable and unuseable. Finally, the interior surface 4" of the molded tube 4 may be corrugated, roughened or otherwise shaped, as shown in FIG. 19, to produce a nail with a higher surface area than a smooth surface. This provides a greater surface area to elute the antibiotic impregnated in the bone cement of the cement nail.

The inventive AIBC IM nail production kit includes at least the molded tube 4, which has an attachment means 4' at one end to allow for attachment of the tube to a conventional bone cement gun 5. The other end of the molded tube is adapted for insertion of a base IM nail or other base support thereinto. The molded tube can come in any desired inner diameter (such as 9, 10, 11, 12, 13, and 14 mm, etc). They can also come in different lengths, however to make manufacturing less expensive a single length tube having indicia on the molded tube indicating where the molded tube may be cut to the desired length before creation of the AIBC coated IM nail. The molded tube should be formed from a material that is compatible with the AIBC, easily holds it shape and is easily removed from the finished, hardened AIBC IM nail. Preferably the material of the molded tube is also inexpensive.

The inventive cement IM nail production kit also includes mold spacers designed to be inserted in the locking screw holes of the IM nail. The spacers allow the IM nail to be properly spaced in the center of the molded tube so that the AIBC can be evenly distributed around the base support within the mold as it is pumped in by the cement gun. The spacers also keep the AIBC from plugging the locking screw holes of the base and/or create locking screw holes in the cement IM nail. This allows the user to avoid having to bore the AIBC out of the locking screw holes. As described above the mold spacers maybe integrally formed into the molded tube if desired.

The inventive AIBC IM nail production kit may also include a supply of AIBC which may be prepared in the conventional manner and loaded into the cement gun. The kit may also include a cement gun and even a specific base IM nail or other support base for the AIBC IM nail. The kit may further include locking screws or other hardware for fixation of the cement IM nail.

The inventive method for forming an antibiotic impregnated bone cement intramedullary nail includes the step of: providing a molded tube having an interior shape and size corresponding to the desired AIBC IM nail, wherein the molded tube also includes an attachment means on one thereof, wherein the attachment means is designed to allow for attachment of the tube to a bone cement gun. The other end of the molded tube adapted for insertion of a base IM nail or other base support thereinto.

The method further includes the step of providing a base IM nail or other base support which will form the base or support for the AIBC IM nail. The base IM nail or other base support may have locking screw holes therethrough.

The method further comprises the step of providing mold spacers, wherein the mold spacers may be small tubes or cylinders that may have an outer diameter equal to the inner diameter of the locking screw holes of the IM nail and the mold spacers may have a length equal to the inner diameter of the molded tube. Alternatively the mold spacers may be integrally formed in the interior of the molded tube.

The method may further includes the step of inserting the mold spacers into the locking screw holes in the base support or base IM nail, wherein the mold spacers protrude about equidistant from either side of the base support or base IM nail.

The method further includes the step of inserting the base IM nail, along with the inserted mold spacers, into the end of the molded tube that is adapted for insertion of a base IM nail thereinto. Alternately, the base support may be inserted by compressing the molded tube so as to separate the integral mold spacers, then the base support may be inserted and the mold spacers inserted into the locking screw holes of the base (if it has any).

The method further includes the optional step of trimming any excess length off from the molded tube, either prior to or after insertion of the base support or base IM nail.

The method further includes the step of attaching the molded tube to a bone cement gun via the attachment means. The attachment step may occur before or after insertion of the base support or base IM nail into the molded tube.

The method further includes the step of pumping AIBC from the cement gun through the attachment means into the interior of the molded tube. The pumping step includes pumping a sufficient amount of AIBC to completely fill the interior of the molded tube and surround the base support or base IM nail. The mold spacers substantially prevent AIBC from entering the any locking screw holes of the base support or base IM nail and/or create locking screw holes in the cement IM nail.

The method may further include the steps of preparing the AIBC and loading the prepared AIBC into the cement gun. These steps may occur at any point before pumping of the AIBC into the molded tube. However, the AIBC will harden and this fact will limit the time frame in when the AIBC may be prepared.

Once the AIBC is pumped fully into the molded tube, the method includes the steps of removing the molded tube from the cement gun and allowing the AIBC to set or harden. Once the AIBC is set or hardened, the method includes the further step of removing the molded tube from the AIBC IM nail. The molded tube may be removed by cutting, tearing, sliding, or any other appropriate means. Once the tube has been removed, the method includes the step of removing the mold spacers from the cement IM nail, thus opening the locking screw holes. However, if the mold spacers are integrally formed into the molded tube, they will generally be automatically removed when the molded tube is removed.

Certain variations on the embodiments described above include: 1) the mold spacers can be other shapes and can allow the AIBC to infiltrate into the locking screw holes, necessitating a bore-out of the holes to accommodate the required locking screws; 2) the mold spacers may be inserted from outside the molded tube through the molded tube and into the locking screw holes, possibly requiring removal of the mold spacers before removal of the molded tube once the AIBC has set or hardened. The base support may also be called the metal IM nail or base IM nail herein. It is to be understood that the disclosure set forth herein is presented in the form of detailed embodiments described for the purpose of making a full and complete disclosure of the present invention, and that such details are not to be interpreted as limiting the true scope of this invention as set forth and defined in the appended claims.

I claim:

1. A kit for forming antibiotic impregnated bone cement (AIBC) intramedullary (IM) nails comprising:
    a molded tube, said molded tube having an interior shape and size corresponding to the desired final AIBC IM nail and including an attachment means at one end thereof to allow for attachment of said molded tube to a conventional bone cement gun, the other end of said molded tube adapted to allow for insertion of a base support or base IM nail thereinto; and
    mold spacers adapted to either:
    1) be inserted into locking screw holes of said base support or base IM nail; said mold spacers allowing said base IM nail to be properly spaced in the center of said molded tube so that AIBC can be evenly distributed around said base IM nail within said molded tube as said AIBC is pumped in by said cement gun; or
    2) form locking screw holes in the final AIBC IM nail when said base support does not have locking screw holes.

2. The kit of claim 1, wherein said molded tube has a length which accommodates a specific base support or base IM nail.

3. The kit of claim 1, wherein said molded tube has a length which is longer than needed to accommodate any specific base support or base IM nail and may be cut to the required length of the desired final AIBC IM nail.

4. The kit of claim 3, wherein said molded tube has indicia thereon to indicate where to cut the molded tube to the desired length.

5. The kit of claim 1, wherein said molded tube has an inner diameter which corresponds to the desired diameter of the final AIBC IM nail.

6. The kit of claim 5, wherein said molded tube has an inner diameter selected from the group consisting of 9, 10, 11, 12, 13, and 14 mm.

7. The kit of claim 1, wherein said molded tube is formed from a material that is: 1) compatible with the AIBC, 2) easily holds it's shape, and 3) is easily removed from the finished, hardened AIBC IM nail.

8. The kit of claim 1, wherein said mold spacers are designed to keep said AIBC from plugging said locking screw holes of said base support or base IM nail.

9. The kit of claim 8, wherein said mold spacers are small tubes or cylinders that have an outer diameter equal to the inner diameter of said locking screw holes of said base support or base IM nail and a length equal to the inner diameter of said molded tube.

10. The kit of claim 8, wherein said mold spacers are integrally formed into said molded tube and extend into the interior of said molded tube far enough to plug the locking screw holes of said base support or base IM nail.

11. The kit of claim 1, further including a supply of AIBC.

12. The kit of claim 1, further including a base support or a base IM nail.

13. The kit of claim 12, wherein said kit includes a base support which is not adapted to be attached to an IM nail insertion handle and said kit further includes a proximal end stub of a conventional IM nail, which is inserted in the proximal end of the molded tube and hardens into the AIBC to provide the AIBC IM nail with a means for attachment to IM nail insertion hardware.

14. The kit of claim 12, wherein said base support comprises a metal strip or metal plate.

15. The kit of claim 12, wherein said base support comprises at least one of the group consisting straight wires, curved wires, coils, flat mesh, and mesh cages.

16. The kit of claim 1, further including a bone cement gun.

17. The kit of claim 1, further including locking screws or other hardware for fixation of the final AIBC IM nail.

18. The kit of claim 1, further including IM nail insertion hardware.

19. A method for forming an antibiotic impregnated bone cement (AIBC) intramedullary (IM) nail including the steps of:
    providing a molded tube, said molded tube having an interior shape and size corresponding to the desired final AIBC IM nail and including an attachment means at one end thereof to allow for attachment of said molded tube to a conventional bone cement gun, the other end of said molded tube adapted to allow for insertion of a base support or base IM nail thereinto;
    providing a base support or base IM nail which will form the support for said AIBC IM nail;
    providing mold spacers adapted to either:
    1) be inserted into locking screw holes of said base support or base IM nail; said mold spacers allowing said base IM nail to be properly spaced in the center of said molded tube so that AIBC can be evenly distributed around said base IM nail within said molded tube as said AIBC is pumped in by said cement gun; or
    2) form locking screw holes in the final AIBC IM nail when said base support does not have locking screw holes;
    providing a bone cement gun loaded with AIBC;
    if said base support or base IM nail has locking screw holes, then inserting said mold spacers into said locking screw holes, wherein said mold spacers protrude substantially equidistant from either side of said base IM nail;
    inserting said base support or base IM nail into said end of said molded tube that is adapted for insertion of said base support or base IM nail thereinto;
    attaching said molded tube to said bone cement gun via said attachment means thereon, wherein said attaching step may occur before or after said step of inserting said base support or base IM nail into said molded tube;
    pumping AIBC from said cement gun through said attachment means into the interior of said molded tube;
    removing said molded tube from said cement gun and allowing said AIBC to set or harden;
    removing said molded tube and said mold spacers from said AIBC IM nail.

20. The method of claim 19, wherein said mold spacers are small tubes or cylinders and said base support or base IM nail has locking screw holes,
    wherein said mold spacers have an outer diameter equal to the inner diameter of said locking screw holes of said base support or base IM and a length equal to the inner diameter of said molded tube, wherein said mold spacers substantially prevent said AIBC from being pumped into said locking screw holes of said base support or base IM; and
    wherein said step of inserting said mold spacers into said locking screw holes occurs before said step of inserting said base support or base IM nail into said molded tube.

* * * * *